United States Patent
Chevion et al.

(10) Patent No.: US 6,426,093 B1
(45) Date of Patent: Jul. 30, 2002

(54) SYNERGISTIC BIOCIDAL ACTIVITY IF TERNARY COMPLEXES OF NEGATIVELY-CHARGED BIOCIDES (COMPONENT A), TRANSITION METAL IONS (COMPONENT B), AND NEUTRAL CHELATORS (COMPONENT C)

(75) Inventors: Mordechai Chevion, Mevasseret Zion; Benzhan Zhu; Svetlana Schechtman, both of Jerusalem, all of (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 09/247,282

(22) Filed: Feb. 9, 1999

Related U.S. Application Data
(60) Provisional application No. 60/074,039, filed on Feb. 9, 1998.

(51) Int. Cl.$^7$ ......................... A01N 55/02; A01N 31/08; A01N 43/42; A01N 59/16
(52) U.S. Cl. ..................... 424/638; 424/617; 424/630; 424/639; 424/641; 424/644; 424/646; 424/649; 424/650; 424/652; 424/654; 424/655; 424/DIG. 6; 514/184; 514/185; 514/190; 514/292; 514/492; 514/494; 514/496; 514/497; 514/498; 514/499; 514/500; 514/501; 514/502; 514/505; 514/731; 514/737; 514/836
(58) Field of Search ........................... 424/DIG. 6, 405, 424/646, 647, 648, 617, 630, 638, 639, 641, 644, 649, 650, 652, 654, 655; 514/184, 185, 292, 492, 502, 731, 737, 836, 496, 497, 498, 499, 500, 501, 505, 494, 190

(56) References Cited

U.S. PATENT DOCUMENTS

| | | | |
|---|---|---|---|
| 3,502,777 A | * 3/1970 | Burkhardt et al. | 514/494 |
| 4,004,006 A | * 1/1977 | Shulman et al. | 514/185 |
| 4,686,211 A | * 8/1987 | Hara et al. | 514/148 |
| 5,338,748 A | * 8/1994 | Wachman et al. | 514/358 |

OTHER PUBLICATIONS

STN/CAS online, file SCISEARCH, Acc. No. 94:455338 (Frey et al., Inorganic Chemistry (1994), vol. 33, No. 15, pp. 3229–3234), Abstract.*
Abbasi, 'Binary and ternary complexes of interest to environmental systems. Part Vi. Interaction of zinc(II) with a mixture of drug' (1980), Polish Journal of Chemistry, vol. 54, Issue 7–8, pp. 1377–83.*
Ranford et al., 'Cytotoxicity and antiviral activity of transition–metal salicylato complexes and crystal structure of bis(diisopropylsalicylato)(1,10–phenanthroline)copper(II)' (1993), J. Chem.Soc.Dalton Trans., pp. 3393–99.*
Sahai et al., 'Intramolecular aromatic ring stacking & structure–stability–activity correlation in ternary complexes of Cu(II) & ZN(II) with some alpha–amino acids & N–bases as primary ligands & plant growth regulators as secondary ligands' (1983), Indian J. Chem., Sect. A, vol. 22A (9), pp. 778–83.*
Patel et al., 'Antimicrobial activity of nickel(II), copper(II) and zinc(II) chelates with 2,2'bipyridylamine and aromatic phenols' (1995), J. Coord. Chem. vol. 36(3), pp. 231–3.*
Poleti et al., 'The thermal behaviour of ternary Co(II), Ni(II) and Cu(II) complexes with phthalate ion and 1,10–phenanthroline or 2.2'–dipyridylamine', Thermochimica Acta, 205 (1992), pp. 225–33.*
Ainscoughe et al., 'Small molecule analogues for the specific metal binding site of lactoferrin. Part 2. Phenolato-complexes of copper (II) and the nature of the charge–transfer transition in the visible region', J.S.C. Dalton (1981), pp. 1701–07.*
Rao et al., 'Kinetics of oxidation of some phenols by iron(III)–1,10–phenanthroline complex'(1978), J. Indian Chem. Soc., vol. LV, pp. 207–10.*
Wulfsberg et al., 'Lewis–base properties of ortho chlorines in copper (II)2,4,6–trichlorophenolates, 4–bromo–2, 6–dichlorophenolates, and 2,6–dichlorophenolates as studied by 35Cl nuclear quadrupole resonance spectroscopy' (1984), Inorganic Chem., vol. 23, No. 6, pp. 715–719 m2.*
Harrod, 'Phenoxo complexes of copper(II)' (1969), Canadian Journal of Chemistry, vol. 47, No. 4, pp. 637–45.*
Database HCAPLUS on STN, American Chemical Society, AN 1984:30871, Sahai, R. et al. 'Intramolecular aromatic ring stacking and structure–stability–activity correlation in ternary complexes of copper(II) and zinc(II) with some alpha–amino acids and N–bases as primary ligands and plant growth regulators as secondary ligands,' abstract, Indian J Chem, Sect. A, 1983, vol. 22A(9), pp. 778–783.
Database HCAPLUS on STN, American Chemical Society, AN 1981–162633, Abbasi, S.A. 'Binary and ternary complexes of interest to environment systems. Part IV. Interaction of zinc(II) with a mixture of drugs.' abstract, Pol. J. Chem., vol. 54(7–8), pp. 1377–1383.
Database HCAPLUS on STN, American Chemical Society, AN 1995:980836, Patel, A.D. et al., 'Antimicrobial activity of nickel(II), copper(II) and zinc(II) chelates with 2,2'–bipridylamine and aromatic phenols.' abstract, J. Coord. Cem., 1995, vol. 36(3), pp. 231–233.

* cited by examiner

Primary Examiner—Jose' G. Dees
Assistant Examiner—Frank Choi
(74) Attorney, Agent, or Firm—Browdy and Neimark

(57) ABSTRACT

A biocidal composition composed of a ternary complex of a negatively-charged biocide, a transition metal ion and chelator has synergistic biocidal effects as compared with a composition of each of the components alone. The chelator is preferably a neutral or positively-charged chelator. The ternary complex may be used for killing or inhibiting the growth of living cells.

10 Claims, 5 Drawing Sheets

SYNERGISTIC BIOCIDAL ACTIVITY IF TERNARY COMPLEXES OF NEGATIVELY-CHARGED BIOCIDES (COMPONENT A), TRANSITION METAL IONS (COMPONENT B), AND NEUTRAL CHELATORS (COMPONENT C)

CROSS-REFERENCE TO RELATED APPLICATIONS

The present application claims priority from U.S. provisional application Ser. No. 60/074,039, filed Feb. 9, 1998, the entire contents of which are hereby incorporated by reference.

BACKGROUND OF THE INVENTION

Public concern is increasing over the contamination of our environment with industrial wastes, including from polyhalogenated compounds. While the effects of acute toxicity are very clear, the effects of chronic exposure to low levels of these chemicals are not well understood. Pentachlorophenol (PCP) is listed as a priority pollutant by the U.S. Environmental Protection Agency because of its toxicity and carcinogenicity. PCP is a general biocide mainly used as a wood preservative. After more than half a century of extensive uses, PCP is considered to be ubiquitously present in the environment and even was found in body fluids of people who were not occupationally exposed to it. Moreover, some of its metabolites have been identified to be carcinogenic and/or mutagenic. Many of these biocides exert their biological damage through the free radical mechanism.

It has been shown that oxidative damage to biological systems is markedly potentiated by the presence of transition metals, especially iron and copper. By virtue of their reactivity with activated oxygen, iron and/or copper can mediate the formation of powerful reactive oxygen species, such as hydroxyl radical, through Fenton reaction. Perhaps for this reason, most cells and organisms handle these metals with great caution; "free" metal is practically absent in biological fluids and the delivery and storage of metals is effected by a series of metal-binding proteins that sequester the metal in such a way as to limit its reactivity.

The evaluation of toxicity of environmental pollutants has been based mainly on the effect of single substances. However, environmental chemicals generally appear as complex mixtures in air, water and soil. It is known that more than one third of sites polluted with organic compounds also contain inorganic pollutants, such as heavy metals. Waste associated with the wood preserving industry is one of the typical cases, since both the organic PCP and inorganic chromated-copper-arsenate wood preservatives have been extensively used. These substances may interact within the mixture to produce combination effects. There is little knowledge on these effects, especially when substances occur at subtoxic concentrations.

In the literature, three classes of combination effects are discussed. They are additive (zero interaction) when the effect of the combination is precisely what is "expected" from the effects of the single compounds; they are synergistic or antagonistic if the response is greater or less than expected. Additive effects are expected in combinations of similar or identical acting chemicals. Every concentration of the single substances will add to the combination's effect. Toxic combination effects may occur from concentrations below the "no observed effect concentration" of single compounds, if the sum of their concentrations exceeds the toxic threshold level. This concept of "concentration addition" is in some countries taken into consideration when threshold limits are defined.

If chemicals have a different mode of toxic action and attack different targets, they are designated as dissimilar chemicals. As long as they act independently, subtoxic concentrations of these substances should not result in toxic combination effects. However, combinations of dissimilar chemicals may interact whereby one chemical alters the biological response of the other in a qualitative or quantitative manner. In this case the combination effects are greater or smaller than predicted from the single compounds. Synergistic or antagonistic effects occur. If single components of a mixture at their no observed effect concentration interact synergistically they should lead to toxic combination effects.

SUMMARY OF THE INVENTION

It has now been discovered that a ternary complex of a negatively-charged biocide (component A), a transition metal ion (component B) and a chelator (preferably a neutral or positively-charged chelator) (component C) has significant biocidal effects on living cells including those of microorganisms, such as bacteria and fungi, cell culture systems, plants and animals. The biocidal effects of the ternary complexes of the three components are synergistic in that the combined biocidal effects are greater than would be expected from the additive effects of each of the components used alone.

Thus, the present invention relates to biocidal compositions comprising such ternary complexes, as well as methods for killing or inhibiting the growth of living cells using an effective amount of such compositions.

BRIEF DESCRIPTION OF THE DRAWINGS

FIG. 1A compares the effect of 0.25 mM pentachlorophenol (PCP), 0.25 mM PCP+16 $\mu$M $Fe(NTA)_2$ (where NTA is nitrilotriacetic acid), and 0.25 mM PCP+16 $\mu$M $Fe(OP)_3$ (where OP is 1,10-phenanthroline) on PCP-induced inhibition of controlled bacterial growth. In FIG. 1B, the effect of $Fe(OP)_3$ at different concentrations are compared to inhibition with $Fe(OP)_3$ or PCP alone. All the incubation mixtures used in FIG. 1B contained bacteria at the initial $OD_{600}$ of 0.2 (1.6×108 cells/ml) in DAVIS medium—represented by x; in the presence of $Fe(OP)_3$ (32 $\mu$M)—represented by open triangles; or PCP (0.25 mM)—represented by open circles; or in the combination of PCP (0.25 mM) and $Fe(OP)_3$ at the concentrations of 8 $\mu$M (small solid square), 16 $\mu$M (medium solid square), and 32 $\mu$M (large solid square).

DETAILED DESCRIPTION OF PREFERRED EMBODIMENTS

Figure 1A:
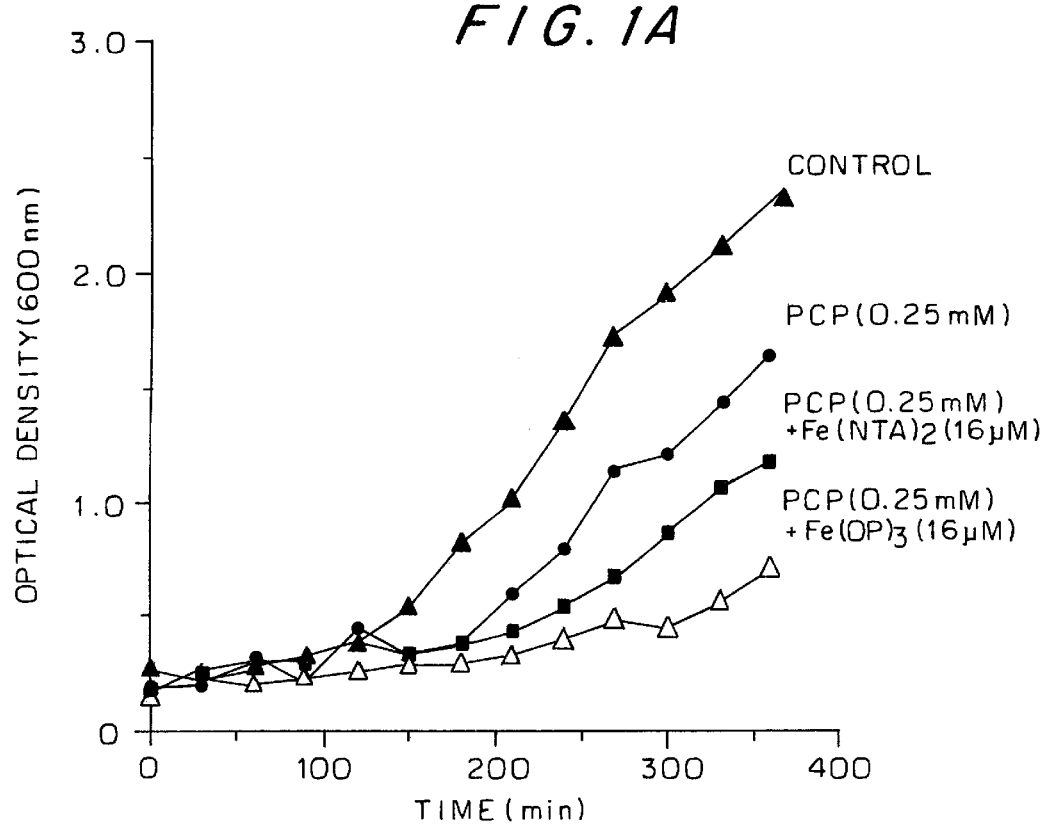
FIGS. 1A and 1B are graphs showing the effect of ferric complexes (FIG. 1A) and different concentrations of $Fe(OP)_3$ (FIG. 1B) on PCP-induced inhibition of controlled bacterial growth.

For the purpose of the present invention, component A may be any negatively-charged biocide. Non-exclusive examples of negatively-charged biocides which may be used for this purpose are the following:

Chlorophenols, such as pentachlorophenol, tetrachlorophenols, trichlorophenols, hexachlorophene, 2,5-dichloro-4-bromophenol and their phenolate forms;

Nitrophenols, such as 2,4-dinitrophenol, 2,4-dinitro-6-methylphenol, 2-(2-butyl)-4,6-dinitrophenol, 2,4,6-trinitrophenol (picric acid), 2-nitro-1-naphthol, 1-nitroso-2-naphthol and their phenolate forms;

Chlorophenoxyacetic acids, such as 2,4-dichlorophenoxyacetic acid (2,4-D), 2,4,5-trichlorophenoxyacetic acid (2,4,5-T);

Catechol and its derivatives, such as catecholamines and tetrachlorocatechol;

Salicylate and its derivatives;

Phthalate and its derivatives;

8-hydroxyquinoline and its derivatives;

Dithiocarbamates;

Thiosemicarbazones;

Pyrophosphates;

Dithiophosphates;

Xanthates;

Pyridinethiones;

β-Diketones;

Long-chain organic acids;

Anionic surface-active agents;

Antituberculous agents, such as Isoniazid, Thiacetazone, Ethambutol and Rifamycin SV; and Chemical agents, such as carbonyl cyanide p-trifluoromethoxyphenylhydrazone (FCCP), 3-chloro-3-butyl-2'-chloro-4'-nitrososalicylanilide (S-13), 4',5-dichloro-3-(p-chlorophenyl)salicylanilide (S-6), 4,5,6,7-tetrachloro-2-trifluoromethylbenzimidazole (TTFB), dicumarol, 2',5-dichloro-4'-nitrosalicylanilide (Bayluscides,), Lipoic acid, and tropolone.

The transition metal ions which may be used as compound B include, but are not limited to:

Iron, copper, chromium, cobalt, nickel, manganese, zinc, platinum, palladium, vanadium, mercury, lead, cadmium, gallium, rare earth metals and lanthanides.

The neutral or positively-charged chelators which are preferably used as component C include, but are not limited to:

1,10-Phenanthroline (OP) and its derivatives, such as 5-phenyl-OP, 5-chloro-OP, 5-nitro-OP, 5-methyl-OP, 4,7-dimethyl-OP, 3,4,7,8-tetramethyl-OP, 4,7-diphenyl-OP=bathophenanthroline and 2,9-dimethyl-OP=neocuproine;

2,2'-Bipyridyl (BP) and its derivatives, such as 4,4'diphenyl-DP;

2,2'-Biquinoline (BQ) and its derivatives;

N,N,N',N'-tetrakis(2-pyridylmethyl) ethylenediamine (TPEN);

2,2': 6'2"-Terpyridine (TP) and its derivatives;

2,4,6-tri(2-pyridyl)-1,3,5-triazine; 3-(2-pyridyl)-5,6-diphenyl-1,2,4-thiazine);

DiSchiff-base ligands, such as N,N'-bis(2-pyridyl-phenyl-methylene)-1,4-butanediamine; and 1-Aminoisoquinolines.

While neutral or positively-charged chelators are preferred, negatively-charged chelators, such as nitrilotriacetic acid (NTA), may also be used. It has been found, however, that the combined effects of the components of the complex are greater when component C is neutral or positively-charged. See FIGS. 1, 2, 4 and 5.

The relative amounts of each of the components of the ternary complex may be determined empirically for any given combination of specific components to determine which relative amounts give the optimum synergistic effect on the biocidal activity. In general, however, for each mole of transition metal ion (component B), 0.05–20 moles of negatively-charged biocide (component A) and 0.05–20 moles of chelator (component C) may be used.

The present invention includes the ternary complexes per se as well as methods of use thereof to kill or inhibit the growth of living cells, such as, for example, bacteria, fungi, cell culture systems, plants (such as weeds and other undesired vegetation), and animals (such as insects, rodents and other pests). An effective amount of the ternary complex is used to permit the desired effect of killing or inhibiting the growth of living cells. Appropriate amounts can readily be determined empirically based on the known effects of the individual components of the complexes. See, for example, the amounts used in the following examples. Dosages of the ternary complex which have an amount of biocide (component A) which is 2–100 fold smaller than the current dosage for the biocide (component A) alone may be used, i.e., 1–50% of current dosage. Depending on the particular ternary complex, the synergistic effect may be sufficient that the amount of biocide in the complex is 0.1% of the effective dosage of the biocide alone. Thus, effective dosages should be effectively determined for any given ternary complex and any given type of living cell to be treated. This can be done by simple and routine experimentation involving testing different amounts of the complex on samples of the cells to be treated.

The ternary complexes of the present invention are substantially amphiphilic in that they are soluble in an aqueous carrier. However, they are sufficiently hydrophobic that, when brought into contact with a hydrophobic cellular environment, such as membranes, the complex will partition into an organic phase, thereby facilitating transport through the membranes and into the cells. For example, the ternary complex pentachlorophenol-iron(II)-1,10-phenanthroline at molar ratio 2:1:3 was found to be water soluble but was, nonetheless, found highly hydrophobic such that it could be partitioned into an organic phase. Each component alone is hydrophilic and remains in the water phase. When pentachlorophenol is substituted by any compound from the list of component A, iron by any metal of component B, and 1,10-phenanthroline by any of the compounds of component C, similar results will be obtained.

EXAMPLES

Example 1

Ternary complex pentachlorophenol-iron(II)-1,10-phenanthroline at molar ratio 2:1:3 was found highly hydrophobic and could be partitioned into organic phase, while each component alone is hydrophilic and remains in the water phase. When pentachlorophenol is substituted by any compound from the list of component A, iron by any compounds of component B, and 1,10-phenanthroline by any compounds of component C, similar results are obtained.

Example 2

Incubation of bacteria (*E. coli*) with polychlorophenols, such as PCP in combination with different positively-charged metal complexes, such as 1,10-phenanthroline-iron $[Fe^{III} (Op)_3]^{3+}$ complex, after 30 minutes showed synergistic cytotoxic effect as measured by colony-forming ability (2% survival), while either PCP (0.5 mM) or $[Fe^{III} (OP)_3]^{3+}$ complex (5 $\mu$M) alone has only marginal effect (>80% survival). The 1,10-phenanthroline-copper $[Cu^{II} (OP)_3]^{2+}$ complex is 100 times more active than the analogous iron complex.

Example 3

Treatment of pea plants with 2,4-D and copper-neocuproine complex showed synergistic growth inhibition effects compared to that treated with either 2,4-D or copper-neocuproine complex, separately.

Example 4

Incubation of bacteria (*E. coli*) with polychlorophenols, such as PCP in combination with different positively-charged metal complexes, such as 1,10-phenanthroline-iron $[Fe^{III} (OP)_3]^{3+}$ complex, after 30 minutes showed significant cellular uptake of both iron and PCP, about 3 times more iron and PCP were transported inside the cell, compared to that when PCP (0.8 mM) or $[Fe^{III} (OP)_3]^{3+}$ complex (8 $\mu$M) was incubated with bacteria, separately.

Example 5

Effect of ferric complexes and concentration of $Fe^{III}$ $(OP)_3$ on PCP-induced inhibition of bacterial growth.

Figure 1B:
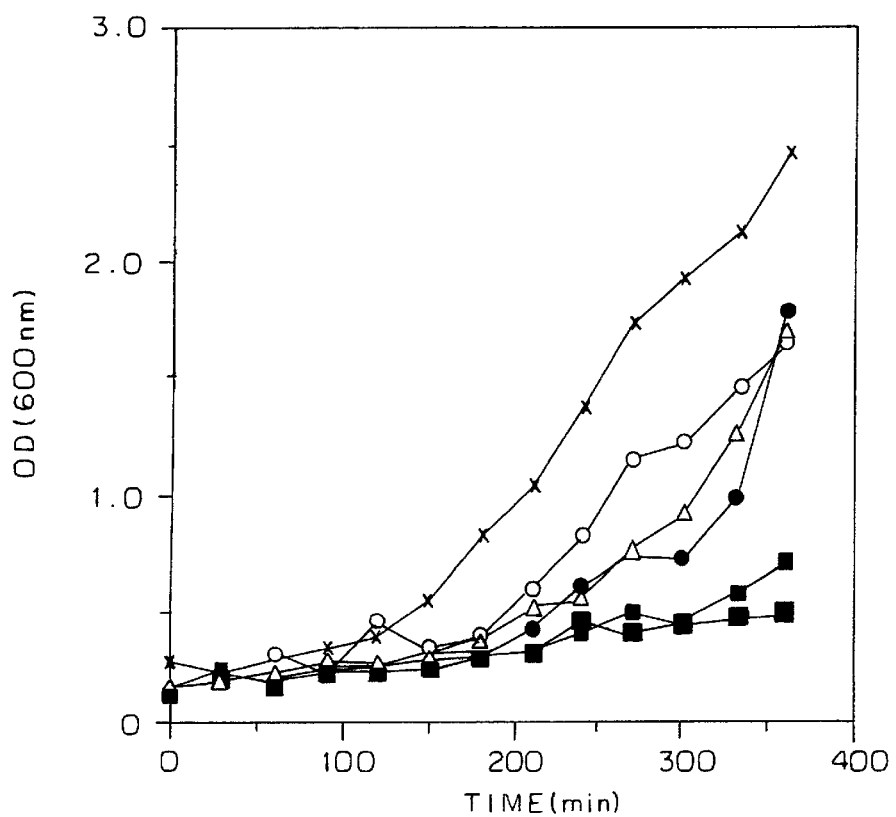

*E. coli* cells, after overnight growth, were inoculated to a final concentration of 0.2 $OD_{600}$ ($1.6 \times 10^8$ cells/ml). PCP was added aseptically to a final concentration of 0.25 mM with or without the ferric complexes to the desired final concentrations. Test flasks were incubated while shaking (at 250 rpm) at 37° C., and bacteria growth monitored spectrophotometrically at 600 nm. Optical density readings were taken every 30 minutes during 7.5 hours of incubation. The growth rate of PCP-treated systems were compared to that of the control (no PCP present). All treatments were repeated at least three times. FIG. 1A shows the effect of ferric complexes on PCP-induced inhibition of bacterial growth, and FIG. 1B shows the effect of the ferric complex $Fe^{III} (OP)_3$ concentration on PCP-induced inhibition of bacterial growth.

Example 6

Effect of ferric and copper complexes on PCP-induced bacterial inactivation and protection against PCP-induced $Fe^{III} (OP)_3$-mediated bacterial cell inactivation.

A sample of bacteria from the stock solution was diluted 100-fold in "reaction buffer" to a final concentration of 0.6 $OD_{600}$ ($4.8 \times 10^6$ cells/ml). Various agents were added to the bacteria following 15 minutes of preincubation at 37° C. Aliquots were removed at indicated time points into "termination buffer" to stop the reaction, and diluted by a factor of 50 to $10^6$. Samples from each dilution were then plated on LB agar and grown overnight at 37° C. Each sample was plated at least five times. The colonies formed were then counted. Survival curves were evaluated from colony counts. Each experiment was repeated at least three times, and the mean values and standard error of triplicates were calculated.

Figure 2:
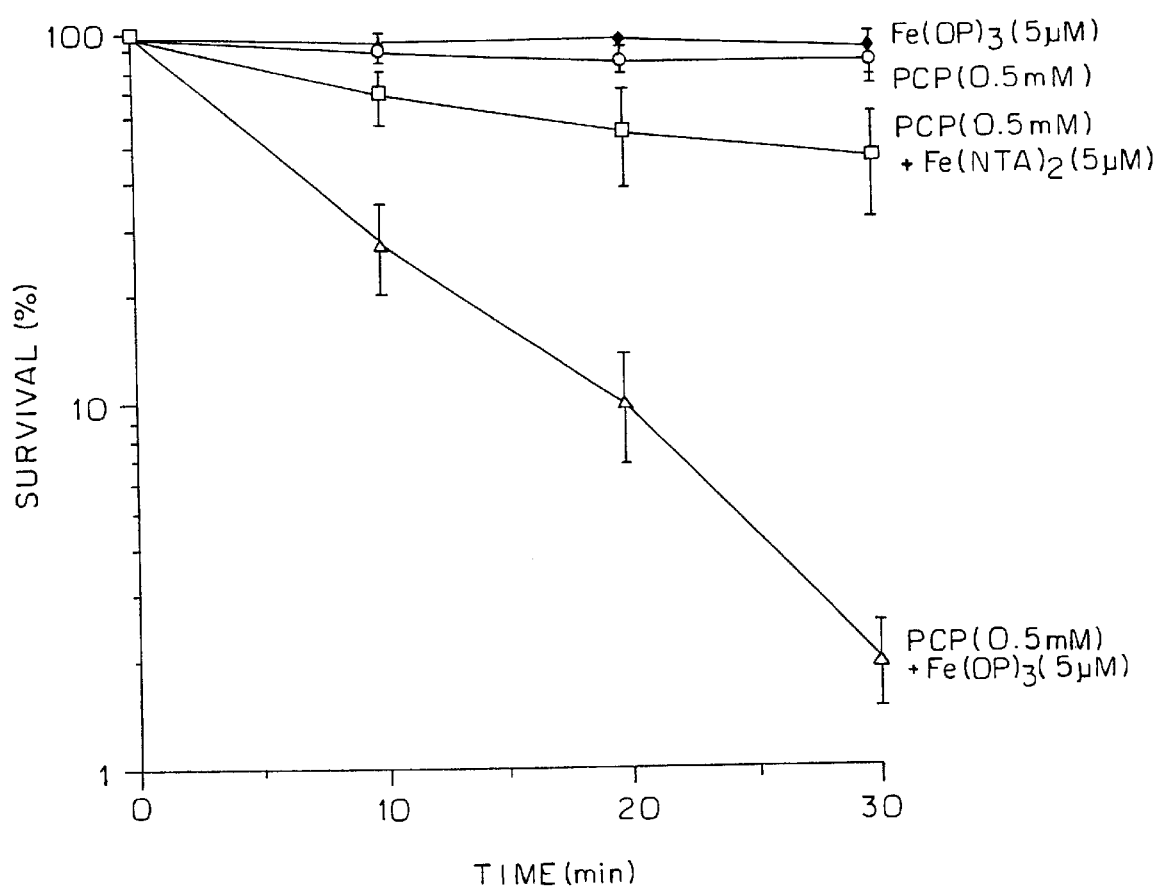
FIG. 2 is a graph showing the effect of ferric complexes on PCP-induced bacterial inactivation. The graph compares the effect of $Fe(OP)_3$ (5 $\mu$M) alone, PCP (0.5 mM) alone, PCP (0.5 mM)+$Fe(NTA)_2$ (5 $\mu$M) and PCP (0.5 mM)+$Fe(OP)_3$ (5 $\mu$M).
Figure 3:
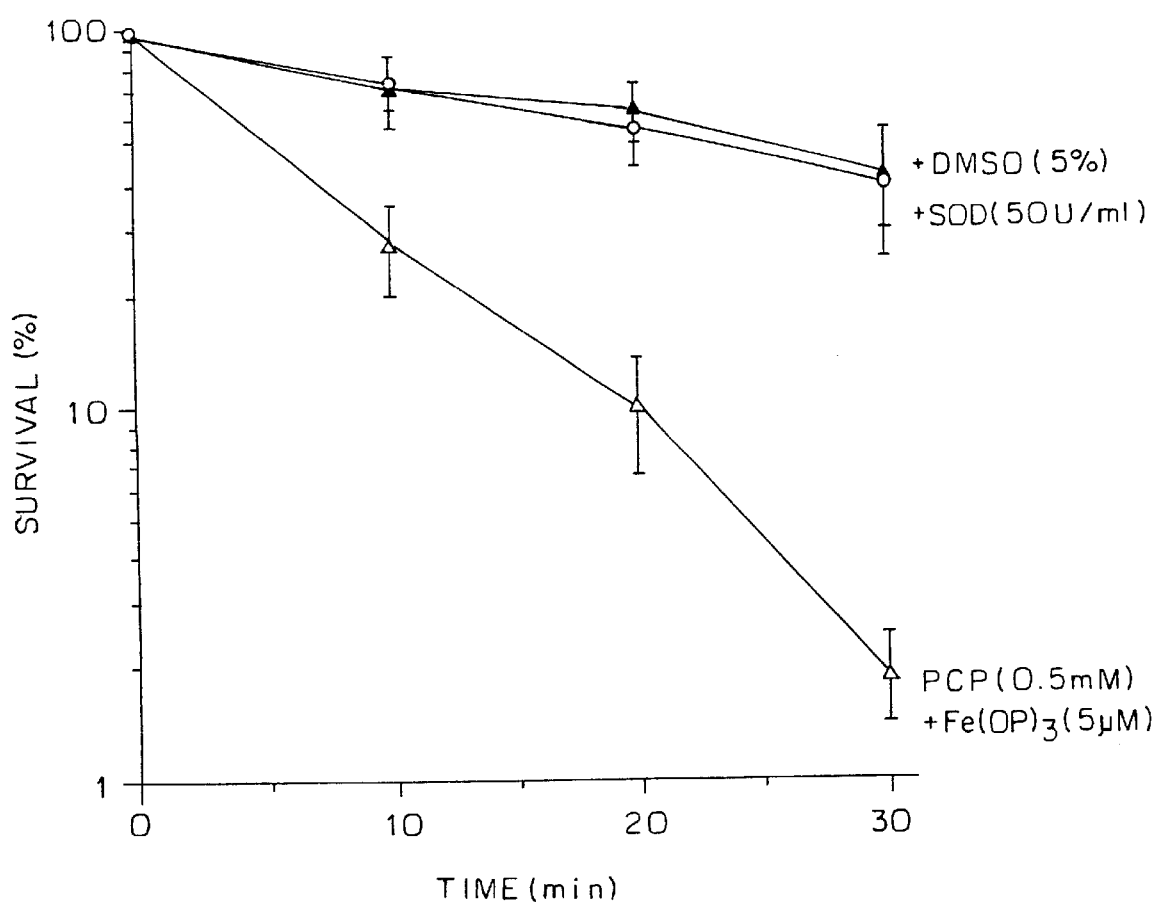
FIG. 3 is a graph showing the protection against PCP induced $Fe^{III}$ $(OP)_3$ mediated bacterial inactivation. The graph compares the use of PCP+DMSO (dimethylsulfoxide) (5%) or PCP+SOD (superoxide dismutase, an enzyme known to protect against free radical-mediated damage) (50 U/ml) as compared with 0.5 mM PCP+5 $\mu$M $Fe(OP)_3$.

FIG. 2 shows the effect of ferric complexes on PCP-induced bacterial inactivation, while FIG. 3 shows a study on protection of bacterial cells against PCP-induced $Fe^{III}$ $(OP)_3$-mediated inactivation. In the experiments shown in FIG. 3, all the incubation mixtures contained glucose (0.5% w/v) and $MgSO_4$ (1 mM) in HEPES buffer (10 mM, pH=7.4), and bacteria ($4.8 \times 10^6$ cells/ml). The cells were exposed to the combination of PCP (0.5 mM) and $Fe(OP)_3$ (5 $\mu$M)—designated open triangles; or with the addition of DMSO (5%)—designated closed triangles; or with SOD (50 U/ml)—designated open circles. The results presented in Table 1, which were obtained using the experimental conditions and methods described above in this example, show the effect of different concentrations of PCP and copper complex and their combinations on the inactivation of *E. coli*.

TABLE 1

The Effect of Different Concentrations of PCP and Copper Complex and Their Combinations on Inactivation of *E. coli*

| Treatments | Survival (%) |
| --- | --- |
| Control | 100 |
| PCP 0.4 mM | 95.6 |
| $Cu^{II} (OP)_2$ 1 $\mu$M | 99.5 |
| PCP 0.4 mM + $Cu^{II} (OP)_2$ 0.05 $\mu$M | 0.1 |
| PCP 0.2 mM + $Cu^{II} (OP)_2$ 0.1 $\mu$M | 0.1 |
| PCP 0.05 mM + $Cu^{II} (OP)_2$ 0.4 $\mu$M | 0.1 |
| PCP 0.02 mM + $Cu^{II} (OP)_2$ 1 $\mu$M | 0.1 |

Example 7

Effect of PCP in intracellular uptake of iron from ferric complexes and the effect of ferric complexes on PCP intracellular accumulation.

Bacterial concentration throughout these experiments was 0.6 $OD_{600}$ ($4.8 \times 10^8$ cells/ml). Experiments were carried out in "reaction buffer" (50 ml final volume) at 37° C. or 4° C. for different periods of time. Different combinations of the compounds tested were added following a 15 minute pre-incubation. At different time points, the reaction was terminated by the centrifugation of the bacterial mixture at 6,000 g at 4° C., where the supernatant was discarded, the cell pellet was washed twice by resuspension in the "reaction buffer" and centrifugation. The cell paste was then frozen at −70° C. Frozen cell paste was thawed and resuspended in 4 ml HEPES buffer (10 mM, pH=7.4), then disrupted by sonication at 4° C. The lysate was centrifuged at 8,000 g for 30 minutes and supernatant was separated from debris for PCP determination.

PCP was extracted by a two-step procedure: acidification of the supernatant samples for PCP precipitation (100 μl of 30% trichloro-acetic (TCA) was added to 1 ml samples) followed by centrifugation in a microcentrifuge to collect the pellet, and subsequent extraction of the substrate from the precipitate by acetonitrile (250 μl). In the debris samples, PCP was extracted by the addition of acetonitrile (500 μl). All the samples were kept in a cold and dark place until analyzed.

PCP was analyzed by high performance liquid chromatography (HPLC) on a LICHROSPHER 100 RP-18 column (4.0×250 mm) with $H_3PO_4$ (11 mM)—acetonitrile (50%) mobile phase. Maximum absorption was detected at 254 nm by a UV detector. The retention time for PCP was 15 minutes. PCP was quantified by comparing the peak area with the area of authentic standard (Xun and Orser, 1991).

Cell volume was calculated, assuming an average cell volume equal to $9.8 \times 10^{-18}$ ml.

Both cytosolic and debris fractions were analyzed for their iron content. For the determination of iron concentration in the cell debris, pellets were dissolved in 0.2 ml of concentrated $HNO_3$ and hydrolized by heating in a boiling water bath for 5 minutes. Sample solutions were then further diluted with double distilled water DDW (previously treated with CHELEX resin) and analyzed for total iron content by atomic absorption.

Figure 4:
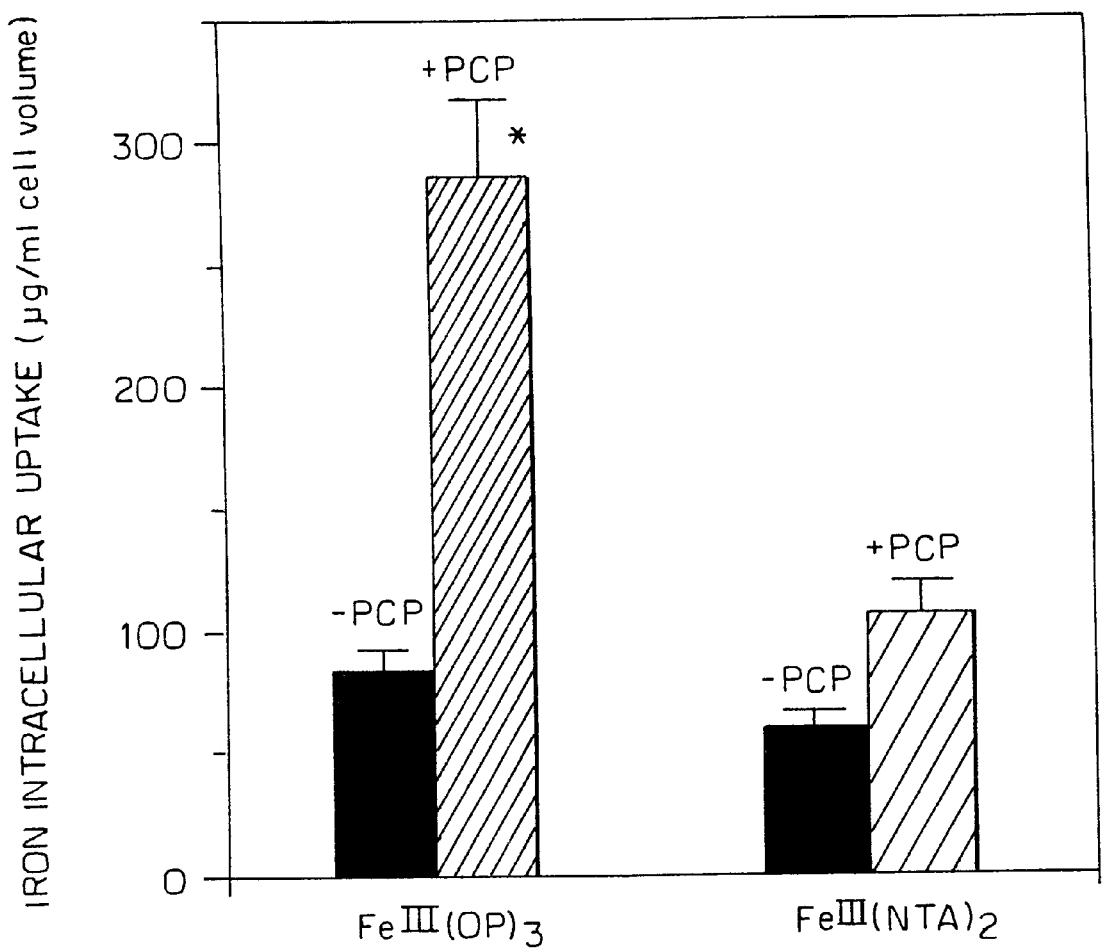
FIG. 4 is a graph showing the effect of PCP on the intracellular uptake of iron from ferric complexes. The iron intracellular uptake of $Fe^{III}(OP)_3$ with and without PCP are compared with that of $Fe^{III}(NTA)_2$ with and without PCP. All the incubation mixtures contained glucose (0.5% w/v) and $MgSO_4$ (1 mM) in HEPES buffer (10 mM, pH=7.4) and bacteria ($4.8\times10^8$ cells/ml). Cells were exposed to $[Fe(OP)_3]^{3+}$ (8 μM) alone or to $[Fe(NTA)_2]^{3+}$ (8 μM) alone—represented by solid bars; or in combination with PCP (0.8 mM)—represented by slashed bars). The symbol * indicates $p<0.05$ as compared to a corresponding treatment in the absence of PCP.
Figure 5:
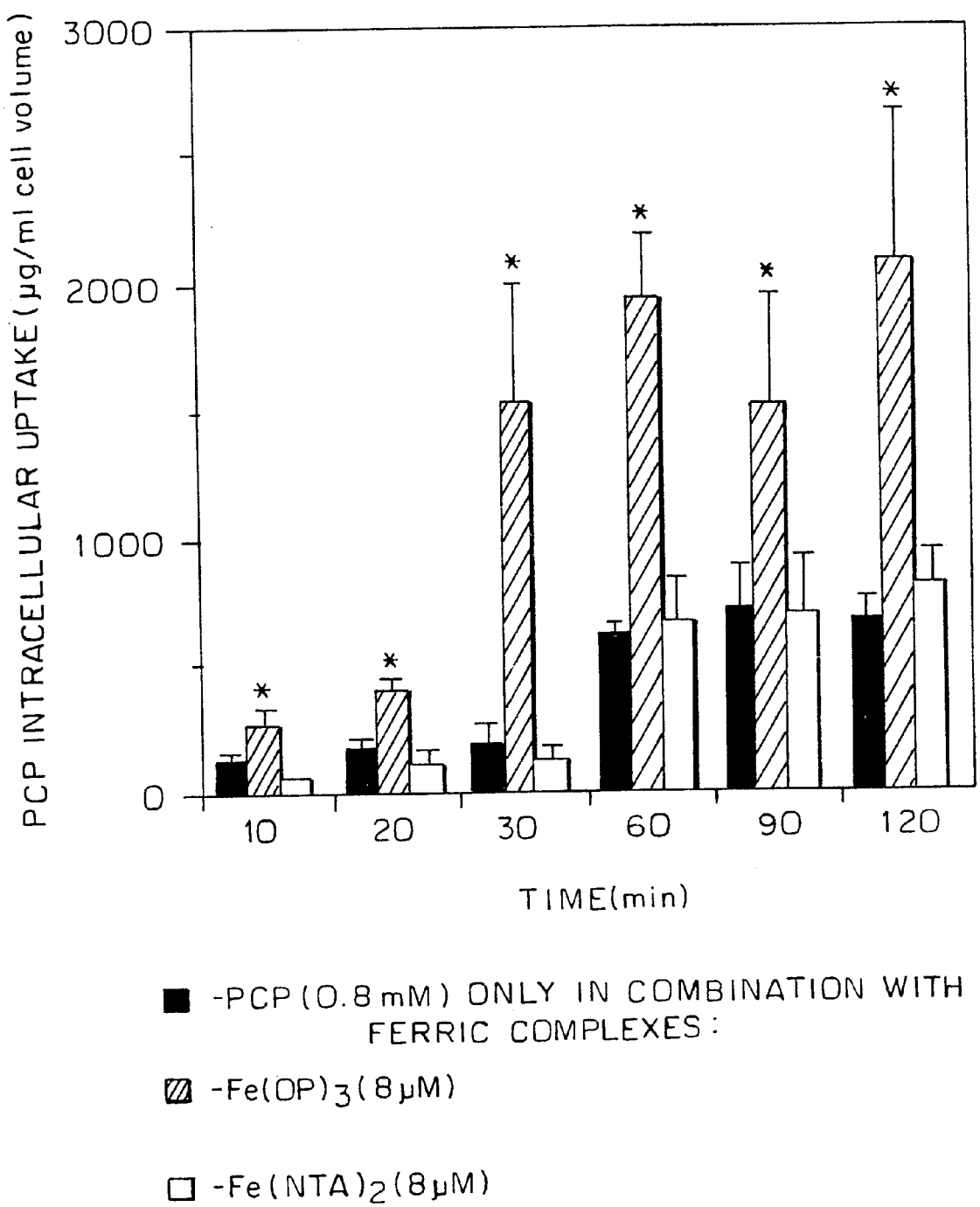
FIG. 5 is a graph showing the effect of ferric complexes on PCP intracellular accumulation. All the incubation mixtures contained glucose (0.5% w/v) and $MgSO_4$ (1 mM) in HEPES buffer (10 mM, pH=7.4) and bacteria ($4.8\times10^8$ cells/ml). Cells were exposed to PCP (0.8 mM) alone or in combination with the ferric complexes $Fe(OP)_3$ (8 μM) or $Fe(NTA)_2$ (8 μM). The symbol * indicates $p<0.05$ as compared with PCP-treated cells.

FIG. 4 is a graph showing the effect of PCP on the intracellular uptake of iron from ferric complexes. FIG. 5 is a graph showing the effect of ferric complexes on PCP intracellular accumulation.

Example 8

Effect of PCP and iron complex on the killing of mast cells.

Bone marrow-derived mast cells (MC-9 line) were obtained from the femora of mice (line C57BL/6). The cells were cultured at 37° C. in humidified atmosphere containing 5% of $CO_2$ in RPMI-1640, supplemented with 10% fetal calf serum, 2 mM L-glutamine, 100 U/ml penicillin, 100 μg/ml streptomycin, and 50 μM β-2-mercaptoethanol. Mast cells were grown (14 days), washed and resuspended in reaction medium (only RPMI-1640) and treated for 30 minutes as indicated above. The survival was determined by the trypan blue method. The results of the effect of PCP and iron complex on mast cell survival are presented in Table 2 below.

TABLE 2

The Effect of PCP and Iron Complex on the Killing of Mast Cells

| Treatments | Survival (%) |
|---|---|
| Control | 100 |
| PCP 0.5 mM | 90.5 |
| $Fe^{II}$ $(OP)_3$ 100 | 95.4 |
| PCP 0.5 mM + $Fe^{II}$ $(OP)_2$ 100 | 4.9 |

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same function can be used; and it is intended that such expressions be given their broadest interpretation.

What is claimed is:

1. A composition comprising a negatively-charged biocide and a ternary complex of said biocide, a transition metal ion, and a neutral or positively charged chelator, said ternary complex consisting essentially of said metal ion and said chelator and said biocide, wherein the negatively-charged biocide is a chlorophenol and the chelator is a 1,10-phenanthroline or derivative thereof, wherein the chelator and transition metal ion form a binary complex which is combined with the negatively-charged biocide, said biocide being present in excess of the stoichiometric ratio of said biocide to said binary complex, to form said composition comprising said biocide and ternary complex, wherein said ternary complex is amphiphilic in that it is soluble in an aqueous carrier but is sufficiently hydrophobic to partition into an organic phase when brought into contact with a hydrophobic cellular environment.

2. The composition of claim 1, wherein the negatively-charged biocide is present in the composition in an excess of at least 5-fold over the stoichiometric ratio of said biocide to the binary complex of the transition metal ion and chelator.

3. The composition of claim 1, wherein said transition metal ion is selected from the group consisting of the ions of iron, copper, chromium, cobalt, nickel, manganese, zinc, platinum, palladium, vanadium, mercury, lead, cadmium, gallium, rare earth metals and lanthanides.

4. The composition of claim 1, further including an aqueous carrier.

5. The composition of claim 1, wherein the combination of components and the ratios thereof are chosen wherein the minimum effective dosage of the negatively-charged biocide in the ternary complex is 0.1–50% of the minimum effective dosage of said biocide alone.

6. The composition of claim 1, wherein the negatively charged biocide is pentachlorophenol, the transition metal ion is iron or copper, and the neutral or positively-charged chelator is 1,10-phenanthroline.

7. A method for killing or inhibiting the growth of living cells, comprising bringing into the vicinity of said cells an effective amount of the composition of claim 1.

8. The method of claim 7, wherein said living cells are those of undesired bacteria, fungi, plants or animals.

9. The method of claim 7, wherein the effective amount includes an amount of the ternary complex in which the amount of the negatively-charged biocide in said ternary complex is 0.1–50% of the dosage required for said biocide alone to be effective.

10. The method of claim 7, wherein the negatively-charged biocide is pentachlorophenol and the concentration of said biocide in the composition which is the vicinity of the cells is 0.02–0.8 mM.

* * * * *